United States Patent
Kim et al.

(10) Patent No.: US 11,636,591 B2
(45) Date of Patent: Apr. 25, 2023

(54) SURFACE IMAGING USING HIGH INCIDENT ANGLE OF LIGHT RAYS

(71) Applicant: Alibaba Group Holding Limited, Grand Cayman (KY)

(72) Inventors: Jin Ryong Kim, San Jose, CA (US);
Hyunjae Gil, Sunnyvale, CA (US);
Stephanie Chan, Sunnyvale, CA (US);
Chen Zhao, Sunnyvale, CA (US)

(73) Assignee: Alibaba Group Holding Limited

( * ) Notice: Subject to any disclaimer, the term of this patent is extended or adjusted under 35 U.S.C. 154(b) by 226 days.

(21) Appl. No.: 16/904,928

(22) Filed: Jun. 18, 2020

(65) Prior Publication Data
US 2021/0398273 A1     Dec. 23, 2021

(51) Int. Cl.
| G06T 7/00 | (2017.01) |
| G06T 9/00 | (2006.01) |
| G06T 7/529 | (2017.01) |
| G06T 7/90 | (2017.01) |

(52) U.S. Cl.
CPC ............ *G06T 7/0012* (2013.01); *G06T 7/529* (2017.01); *G06T 7/90* (2017.01); *G06T 2207/30088* (2013.01)

(58) Field of Classification Search
CPC ......... G06T 7/0012; G06T 7/90; G06T 7/529; G06T 2207/30088; G06T 7/70; G06T 2207/10101; G06T 2207/20024; G02B 21/361; G02B 21/0032; G02B 23/2484; G02B 23/26
See application file for complete search history.

(56) References Cited

U.S. PATENT DOCUMENTS

| 5,836,872 | A  | 11/1998 | Kenet et al. | |
| 6,023,637 | A  | 2/2000 | Liu et al. | |
| 6,937,886 | B2 | 8/2005 | Zavislan | |
| 7,309,335 | B2 | 12/2007 | Altshuler et al. | |
| 8,154,612 | B2 | 4/2012 | Quan et al. | |
| 8,366,622 | B2 | 2/2013 | Slayton et al. | |
| 8,923,954 | B2 | 12/2014 | Herman | |
| 9,042,967 | B2 | 5/2015 | Dacosta et al. | |
| 9,427,187 | B2 | 8/2016 | Gilbert | |
| 10,098,545 | B2 | 10/2018 | Nakajima et al. | |
| 2011/0304705 | A1 | 12/2011 | Kantor et al. | |
| 2020/0259982 | A1* | 8/2020 | Bardagjy | ............... H04N 5/238 |
| 2020/0345293 | A1* | 11/2020 | Ras | ....................... A61B 5/0082 |
| 2020/0375466 | A1* | 12/2020 | Ras | ....................... A61B 5/0077 |

\* cited by examiner

*Primary Examiner* — Vu Le
*Assistant Examiner* — Winta Gebreslassie
(74) *Attorney, Agent, or Firm* — Lee & Hayes, P.C.

(57) ABSTRACT

A plurality of light sources placed at one end of a surface imaging system may generate and direct light rays to be incident onto a surface to be detected at high incident angles that are greater than or equal to a predetermined angle threshold, the predetermined angle threshold may be set to ensure that images of the surface to be detected that have at least a predetermined degree of contrast are to be obtained. An image sensor that is placed at another end of the surface imaging system may collect light rays reflected from the surface to be detected to form a first image of the surface to be detected.

17 Claims, 5 Drawing Sheets

SURFACE IMAGING USING HIGH INCIDENT ANGLE OF LIGHT RAYS

BACKGROUND

Surface imaging is a technology that captures an image of the morphology of a surface, and detects surface texture, and defects, for example, on the surface. For example, owing to an increasing attention of hair loss and scalp diseases, a demand for scalp devices that are capable of capturing images of scalp surfaces for diagnosing scalp conditions is growing. Although existing scalp devices may produce high-quality images of a scalp surface, detailed textures and colorations of the scalp surface may still fail to be captured in the images. Without the knowledge of detailed information of a surface (e.g., detailed textures and colorations of a scalp surface), an analysis of the morphology of the surface may be hard to performed or may be incomplete.

SUMMARY

This summary introduces simplified concepts of surface imaging, which will be further described below in the Detailed Description. This summary is not intended to identify essential features of the claimed subject matter, nor is it intended for use in limiting the scope of the claimed subject matter.

This disclosure describes example implementations of surface imaging. In implementations, a plurality of light sources that are placed at one end of a surface imaging system may generate and direct light rays to be incident onto a surface to be detected at high incident angles that are greater than or equal to a predetermined angle threshold. In implementations, the predetermined angle threshold may be set to ensure that images of the surface to be detected that have at least a predetermined degree of contrast are to be obtained. In implementations, an image sensor that is placed at another end of the surface imaging system may collect light rays reflected from the surface to be detected to form a first image of the surface to be detected.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Example Environment

Figure 1:
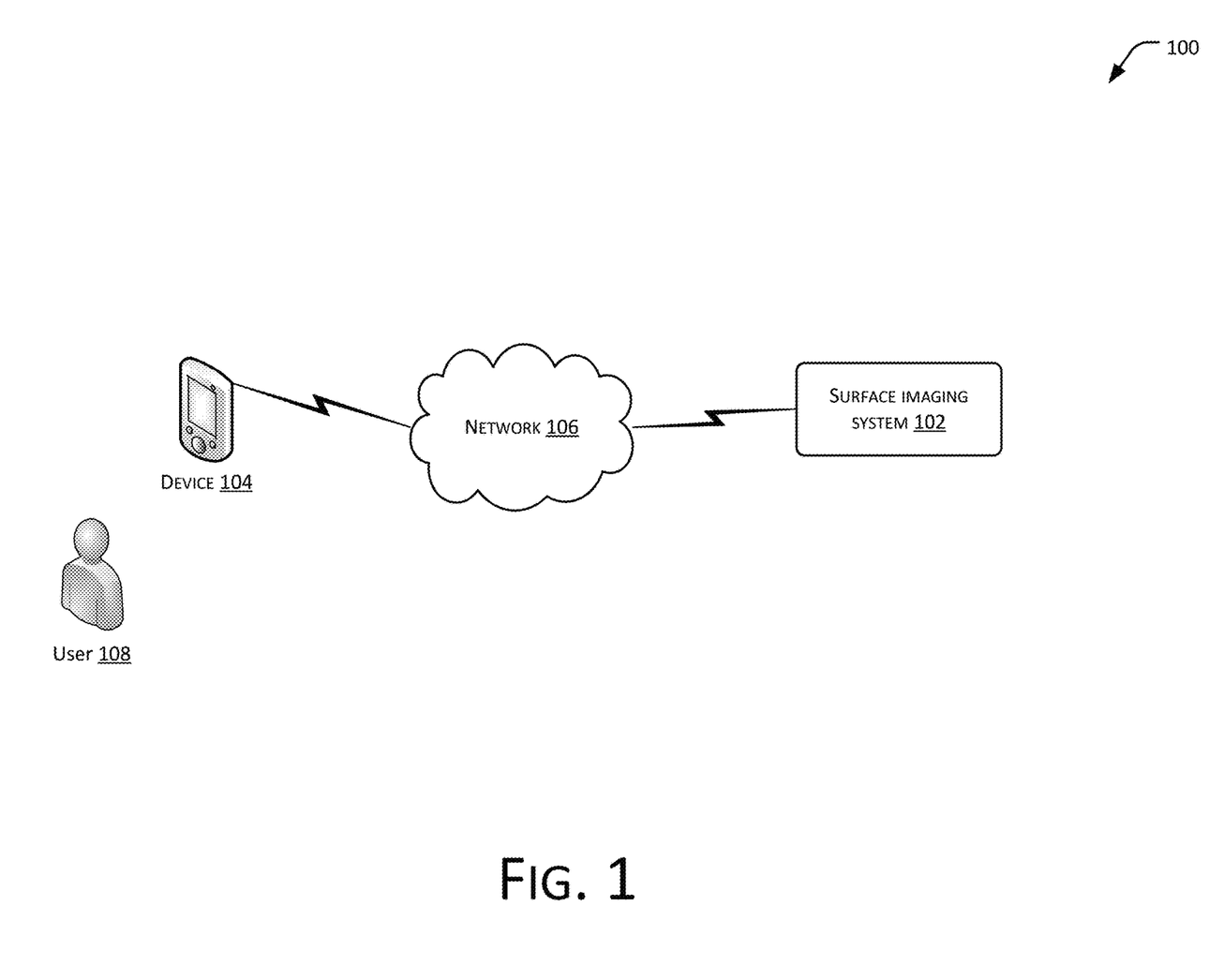
FIG. 1 illustrates an example environment in which a surface imaging system may be used.

FIG. 1 illustrates an example environment 100 usable to implement a surface imaging system. The environment 100 may include a surface imaging system 102. In this example, the surface imaging system 102 is described to exist as an individual entity or device. In some instances, some or all of the functions of the surface imaging system 102 may be included in or provided by one or more computing devices 104, which are connected and communicated via a network 106. In other instances, the surface imaging system 102 may communicate data with the one or more computing devices 104 via the network 106.

In implementations, each of the computing devices 104 may be implemented as, but not limited to, a desktop computer, a notebook or portable computer, a handheld device, a netbook, an Internet appliance, a tablet or slate computer, a mobile device (e.g., a mobile phone, a personal digital assistant, a smart phone, etc.), a server computer, etc., or a combination thereof.

The network 106 may be a wireless or a wired network, or a combination thereof. The network 106 may be a collection of individual networks interconnected with each other and functioning as a single large network (e.g., the Internet or an intranet). Examples of such individual networks include, but are not limited to, telephone networks, cable networks, Local Area Networks (LANs), Wide Area Networks (WANs), and Metropolitan Area Networks (MANs). Further, the individual networks may be wireless or wired networks, or a combination thereof. Wired networks may include an electrical carrier connection (such a communication cable, etc.) and/or an optical carrier or connection (such as an optical fiber connection, etc.). Wireless networks may include, for example, a WiFi network, other radio frequency networks (e.g., Bluetooth®, Zigbee, etc.), etc.

In implementations, the surface imaging system 102 may be used by a user 108 to capture an image of a surface of an object. After obtaining the image of the surface, the surface imaging system 102 may present the image to the user 108 via a display of the surface imaging system 102. Alternatively, the surface imaging system 102 may transmit the image to a device (e.g., the computing device 104) of the user 108, which then presents the image to the user 108 through a particular application that is associated with the surface imaging system 102 and installed in the device (e.g., the computing device 104) of the user 108. In implementations, the user 108 may manipulate the image, and further control the surface imaging system 102 to capture another image by changing one or more parameters of the surface imaging system 102.

Example Surface Imaging System

Figure 2:
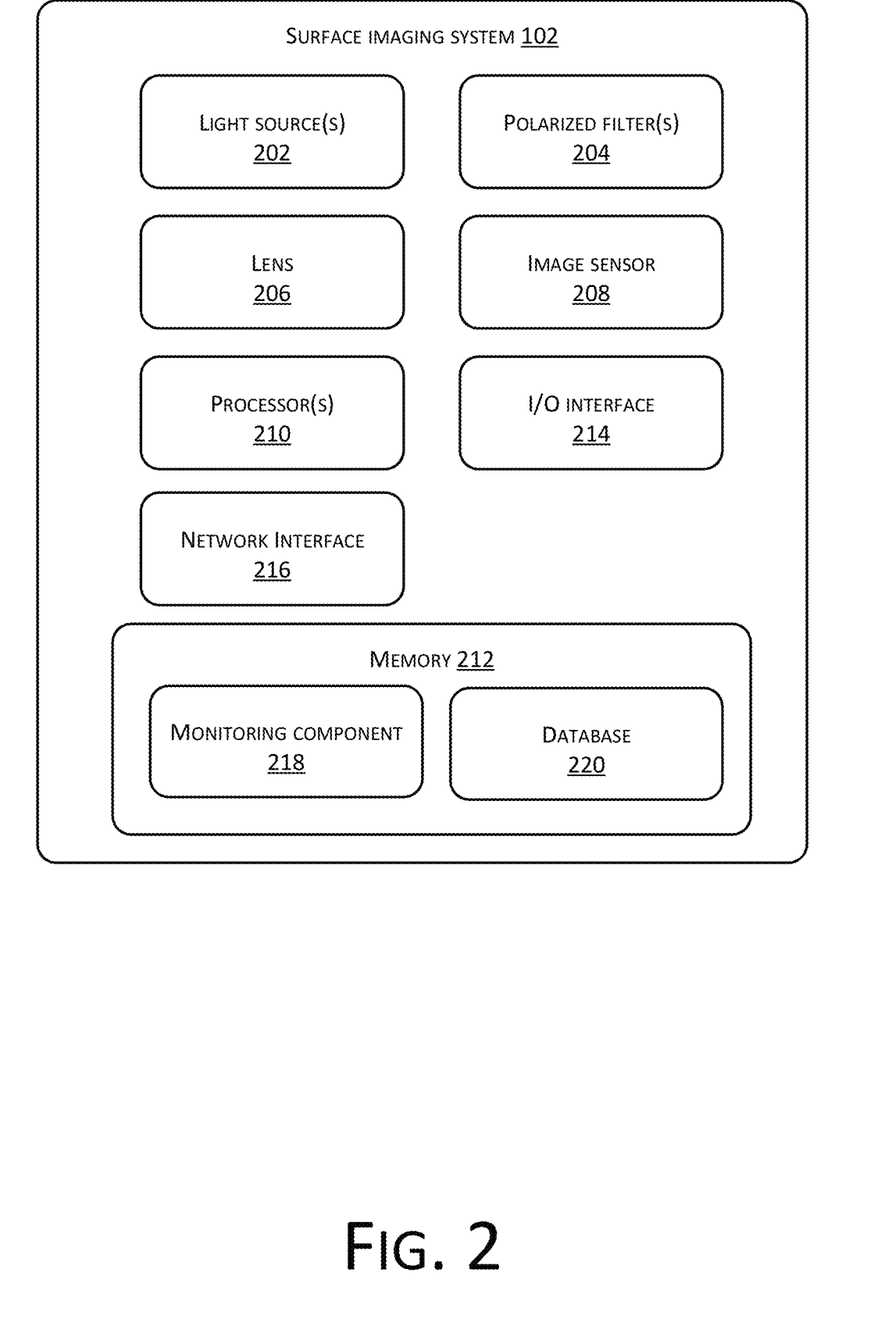
FIG. 2 illustrates the example surface imaging system in more detail.

FIG. 2 illustrates the surface imaging system 102 in more detail. In implementations, the surface imaging system 102 may include, but is not limited to, one or more light sources 202, one or more polarized filters 204, a lens 206, and an image sensor 208. In implementations, the surface imaging system 102 may further include one or more processors 210, memory 212, an input/output (I/O) interface 214, and/or a network interface 216. In implementations, some of the functions or components of the surface imaging system 102 (for example, the one or more processors 210) may be implemented using hardware, for example, an ASIC (i.e., Application-Specific Integrated Circuit), a FPGA (i.e., Field-Programmable Gate Array), and/or other hardware. In this example, the surface imaging system 102 may exist as a separate entity which may or may not be associated with a device such as the computing device 104. In some instances, some of the functions of the surface imaging system 102 may be included in a device such as the computing device 104.

In implementations, the processors 210 may be configured to execute instructions that are stored in the memory 212, and/or received from the input/output interface 214, and/or the network interface 216. In implementations, the processors 210 may be implemented as one or more hardware processors including, for example, a microprocessor, an application-specific instruction-set processor, a physics processing unit (PPU), a central processing unit (CPU), a graphics processing unit, a digital signal processor, a tensor processing unit, a video processor, an image processor, etc. Additionally or alternatively, the functionality described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), etc.

The memory 212 may include computer readable media in a form of volatile memory, such as Random Access Memory (RAM) and/or non-volatile memory, such as read only memory (ROM) or flash RAM. The memory 204 is an example of computer readable media.

The computer readable media may include a volatile or non-volatile type, a removable or non-removable media, which may achieve storage of information using any method or technology. The information may include a computer readable instruction, a data structure, a program module or other data. Examples of computer readable media include, but not limited to, phase-change memory (PRAM), static random access memory (SRAM), dynamic random access memory (DRAM), other types of random-access memory (RAM), read-only memory (ROM), electronically erasable programmable read-only memory (EEPROM), quick flash memory or other internal storage technology, compact disk read-only memory (CD-ROM), digital versatile disc (DVD) or other optical storage, magnetic cassette tape, magnetic disk storage or other magnetic storage devices, or any other non-transmission media, which may be used to store information that may be accessed by a computing device. As defined herein, the computer readable media does not include any transitory media, such as modulated data signals and carrier waves.

In implementations, the one or more light sources 202 may be placed at an end or an edge of the surface imaging system 102 at which a surface to be detected is placed. In implementations, each light source 202 include one or more lighting emitting sources such as light emitting diodes (LEDs). In case when multiple lighting emitting sources are included in the light source 202, the lighting emitting sources may have different light frequencies, for example, frequencies of different colors (red, green, and blue, etc.). In implementations, each light source 202 may include a source emitting light rays of a frequency that can be tuned or altered electronically.

In implementations, some of the one or more polarized filters 204 may be placed in front of the one or more light sources 202, i.e., between the one or more light sources 202 and a surface to be detected. Additionally or alternatively, some of the one or more polarized filters 204 may further be placed between the lens 206 and the surface to be detected. In implementations, the lens 206 may be an optical or microscopic lens that is capable of converging or focusing light rays reflected or scattered from the surface to be detected onto the image sensor 208.

In implementations, the image sensor 208 may include a CMOS image sensor or any other image sensor that is capable of capturing images. In implementations, the image sensor 208 may collect the light rays reflected or scattered from the surface to be detected to form an image of the surface to be detected. In implementations, the image sensor 208 may send data of the image to the one or more processors 210 for processing, send the data of the image to the memory 212 for storage, and/or send the data of the image to a device (such as the computing device 104) of a user via the network interface 216.

Although in this example, exemplary hardware components are described in the surface imaging system 102, in other instances, the surface imaging system 102 may further include other hardware components and/or other software components such as program units to execute instructions stored in the memory 212 for performing various operations. For example, the surface imaging system 102 may further include a monitoring component 218 configured to enable a user to review the images of the surface to be detected, and receive instructions from the user. Additionally, the surface imaging system 102 may further include a database 220 storing data of images that are obtained by the surface imaging system 102.

Figure 3:
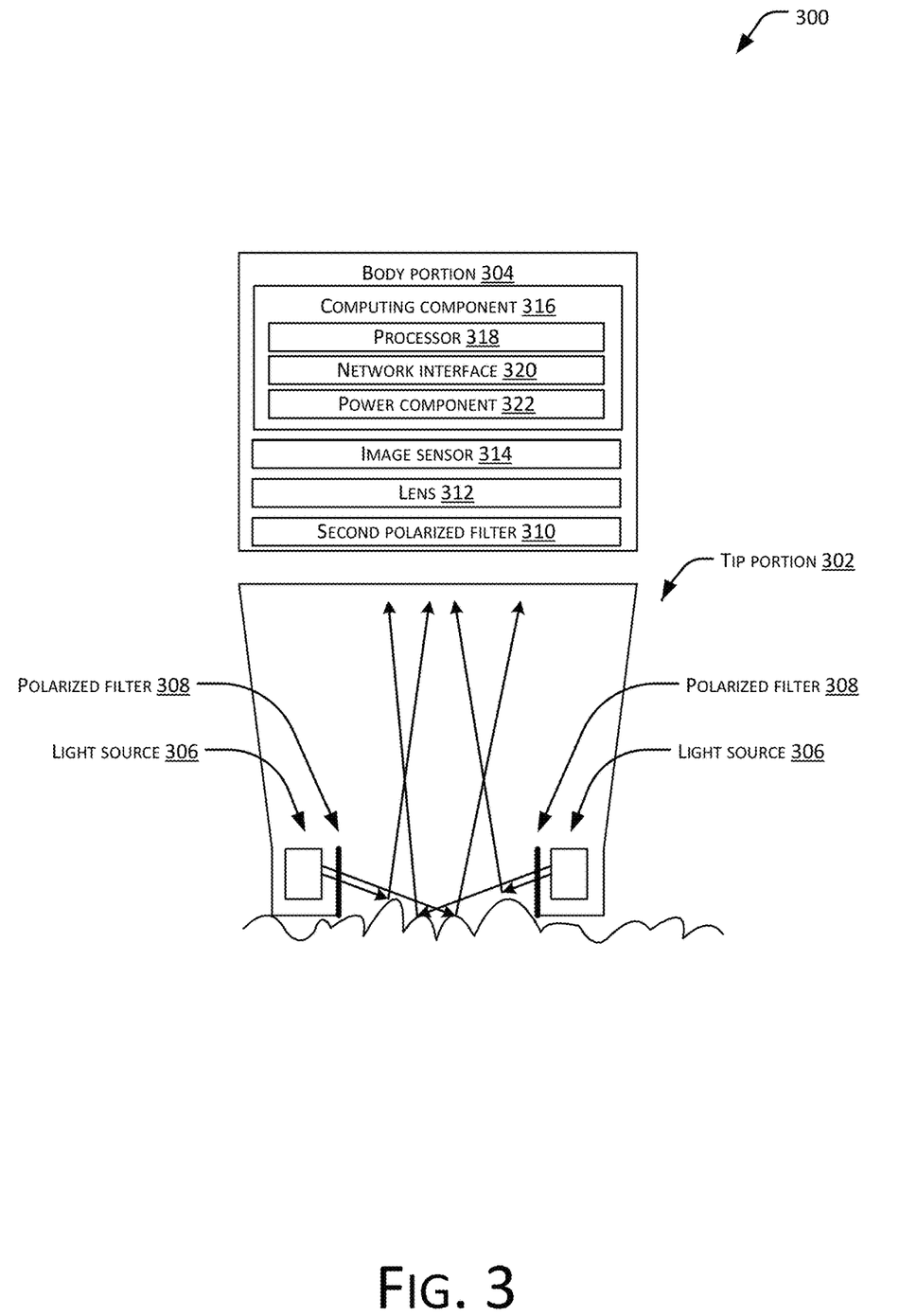
FIG. 3 illustrates an example structure of the surface imaging system.

By way of example and not limitation, FIG. 3 shows an example structure 300 of the surface imaging system 102. Although in this example, an exemplary structure of the surface imaging system 102 is provided, the surface imaging system 102 may have a structure that is different from the example structure 300 as shown herein, which may depend on a plurality of factors. In implementations, the plurality of factors may include, but are not limited to, a type of a surface to be detected, an amount of area of the surface to be detected, properties of components (such as light sources, polarized filters, lens, image sensor, etc.) of the surface imaging system 102, etc. In this example, the surface imaging system 102 is described to capture an image of a skin surface, such as a scalp surface, to detect textures and colorizations of the scalp surface, for example.

As shown in FIG. 3, the structure 300 of the surface imaging system 102 may include two portions, namely, a tip portion 302 and a body portion 304. In implementations, the tip portion 302 may include a plurality of light sources 306, and a first plurality of polarized filters 308. In implementations, the plurality of light sources 306 may be deployed at an end or an edge of the tip portion 306 that faces a surface to be detected, and the first plurality of polarized filters 308 may be separately deployed between the plurality of light sources 306 and the surface to be detected. Light rays generated by a light source 306 may pass through a corresponding polarized filter 308, and may then be incident on the surface to be detected.

In implementations, the body portion 304 may include a second polarized filter 310, a lens 312, and an image sensor 314. In implementations, light rays reflected or scattered from the surface to be detected may pass through the second polarized filter 310, and may be converged by the lens 312 onto the image sensor 314.

In implementations, the body portion 304 may further include a computing component 316, which may include, but is not limited to, a processor 318, a network interface 320, and a power component 322. The image sensor 314 may be connected to the computing component 316, and communicate data (such as image data, etc.) with the computing component 316. In implementations, the computing component 316 may process and analyze data of the image of the surface to be detected transmitted by the image sensor 314, and may transmit the data of the image of the surface to be detected to a device (such as the computing device 104) of a user or an associated application installed in the device, to allow the user to view and manipulate the data of the image.

In some instances, the associated application may further enable the user to control or send an instruction to the surface imaging system 102 to change one or more settings or parameters of the surface imaging system 102. Examples of changing the one or more settings or parameters of the surface imaging system 102 may include, but are not limited to, changing intensities of the plurality of light sources 306, changing angles of incidence of the plurality of light sources 306 onto the surface to be detected, changing an orientation of polarization of the first plurality of polarized filters 308 and/or the second polarized filter 310, etc., to obtain another image of the surface to be detected.

Example Methods

Figure 4:
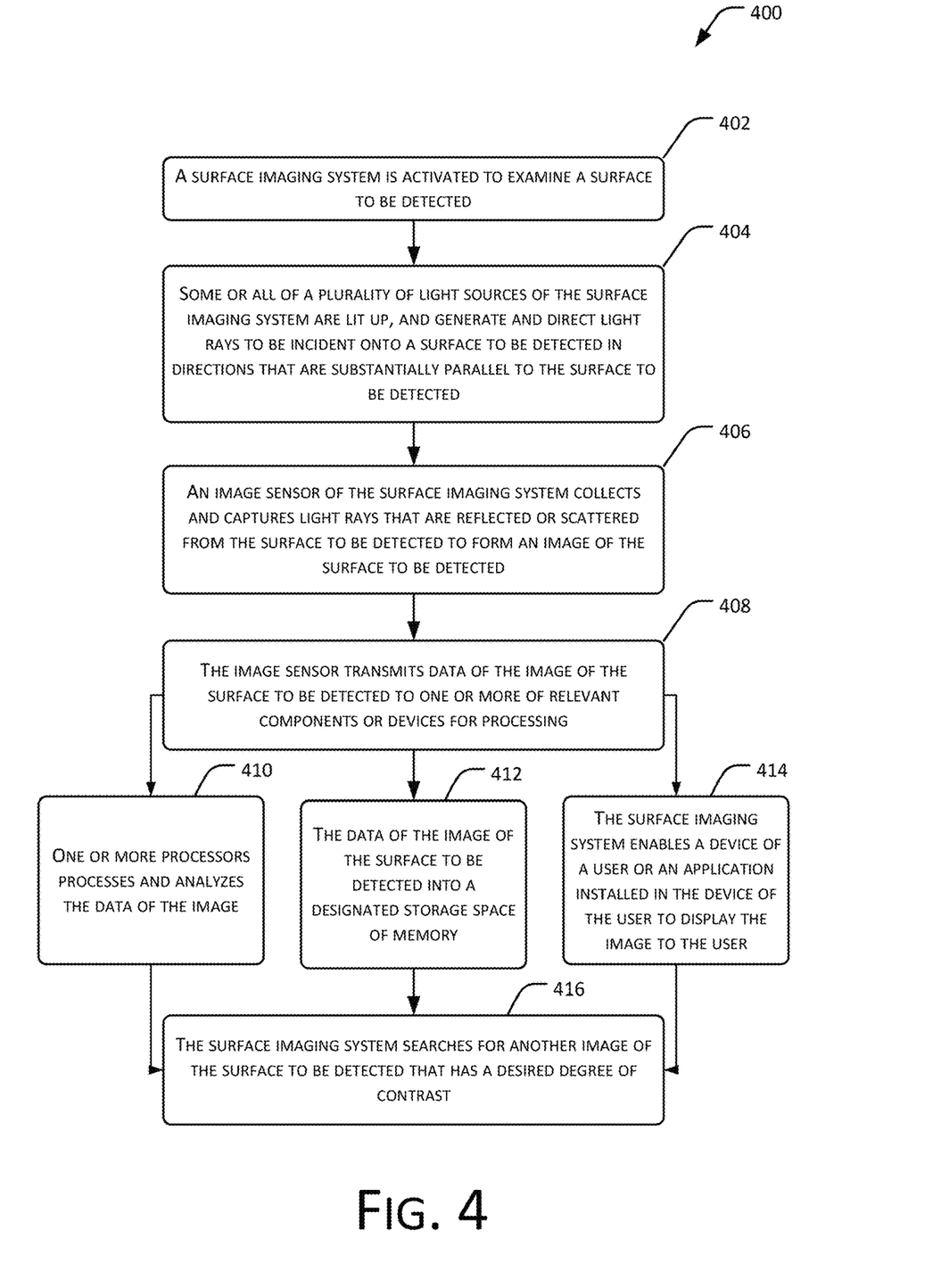
FIG. 4 illustrates an example method of surface imaging.

FIG. 4 shows a schematic diagram depicting an example method of surface imaging. The method of FIG. 4 may, but need not, be implemented in the environment of FIG. 1, and using the systems of FIG. 2 and FIG. 3. For ease of explanation, a method 400 is described with reference to FIGS. 1-3. However, the method 400 may alternatively be implemented in other environments and/or using other systems.

The method 400 is described in the general context of computer-executable instructions. Generally, computer-executable instructions can include routines, programs, objects, components, data structures, procedures, modules, functions, and the like that perform particular functions or implement particular abstract data types. Furthermore, each of the example methods are illustrated as a collection of blocks in a logical flow graph representing a sequence of operations that can be implemented in hardware, software, firmware, or a combination thereof. The order in which the method is described is not intended to be construed as a limitation, and any number of the described method blocks can be combined in any order to implement the method, or alternate methods. Additionally, individual blocks may be omitted from the method without departing from the spirit and scope of the subject matter described herein. In the context of software, the blocks represent computer instructions that, when executed by one or more processors, perform the recited operations. In the context of hardware, some or all of the blocks may represent application specific integrated circuits (ASICs) or other physical components that perform the recited operations.

Referring back to FIG. 4, at block 402, the surface imaging system 102 may be activated to examine a surface to be detected.

In implementations, the surface imaging system 102 may be powered on. For example, a user (e.g., the user 108) may power up the surface imaging system 102, or may input a command to a device (e.g., the computing device 104) of the user 108, which may send an instruction to the surface imaging system 102 to wake up the surface imaging system 102 from a sleep mode to an active mode. In implementations, the surface to be detected may be any surface of an object that is under investigation. By way of example and not limitation, the surface to be detected may include a skin surface of a living entity, such as a scalp surface of a human. In implementations, the surface to be detected may be partially transparent to a certain range of light frequencies, different light frequencies of the certain range of light frequencies leading to different degrees of transparency of the surface to be detected.

At block 404, some or all of the plurality of light sources 202 of the surface imaging system 102 may be lit up, and generate and direct light rays to be incident onto a surface to be detected in directions that are substantially parallel to the surface to be detected.

In implementations, after the surface imaging system 102 is powered on, some or all of the plurality of light sources 202 may be powered on, and emit light rays onto a surface to be detected. In implementations, the light rays emitted from the light sources 202 may pass through the polarized filters 204 that are placed in front of the light sources 202 before landing onto the surface to be detected. In implementations, the polarized filters 204 may be set to allow a particular orientation of polarization of the light rays to pass through.

In implementations, the light sources 202 may generate and direct light rays to be incident onto a surface to be detected at high incident angles. By way of example and not limitation, the light sources 202 may generate and direct light rays to be incident onto a surface to be detected at angles that are greater than or equal to a predetermined angle threshold (e.g., 88°, 89°, etc.). In implementations, the predetermined angle threshold may be set to ensure that images of the surface to be detected that have at least a predetermined degree of contrast (such as 0.7, 0.8, 0.9, 0.95, etc.) are to be obtained. In implementations, a degree of contrast may be calculated or defined using a Weber contrast, an RMS contrast, Michelson contrast, or any other user-defined contrast that reflects an amount of pixel differences between neighboring pixels in an image.

Figure 5:
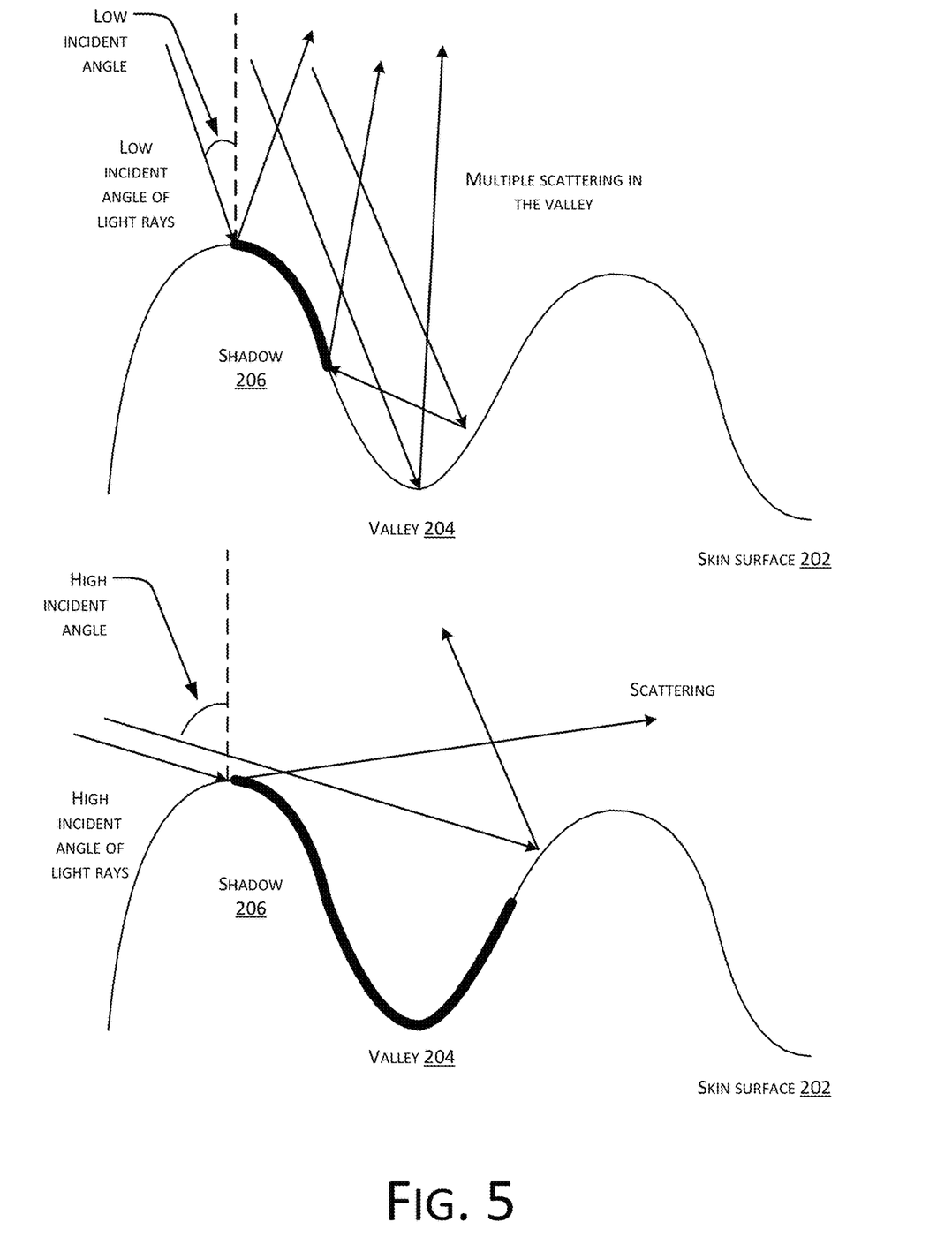
FIG. 5 illustrates example scenarios of different incident angles of light ray.

In implementations, when the light rays generated by the light sources 202 are incident onto the surface to be detected, geometric shadows (which are shadowed areas generated by the light rays due to a geometric shape of the surface to be detected that is not completely flat) are formed. FIG. 5 shows geometric shadowing on a skin surface 202 using two different incident angles of light rays. A low incident angle of light rays may be configured by placing a light source relatively vertical to the skin surface 202. This generally makes multiple orders of scattering from one side of a valley 204 of the surface 202, yielding a limited amount of geometric shadows 206. On the other hand, a high incident angle of light rays can be configured by placing the light source relatively horizontal to the skin surface 202. This generally makes a less scattering of the light rays, including backscattering, and thus creates a higher amount of geometric shadows 206 in the valley 204 of the skin surface 202. In other words, the geometric shadows may take place in deep areas of valleys of the surface to be detected, as upper parts of the valleys of the surface to be detected are illuminated by the light rays with a high incident angle, and the curvature geometry of the surface to be detected make the light rays with the high incident angle be not scattered to the deep areas of the surface to be detected as shown in FIG. 5. Due to the high incident angle, an amount of geometric shadows is relatively large, leading to a higher degree of contrast that provides details (such as textures, colorizations, etc.) of the surface.

At block 406, the image sensor 208 may collect and capture light rays that are reflected or scattered from the surface to be detected to form an image of the surface to be detected.

In implementations, after the light rays that are generated or emitted by the plurality of light sources 202 are incident on the surface to be detected, some light rays may be reflected or scattered by the surface to be detected due to reflection or diffuse reflection. In implementations, some of these light rays may then pass through a polarized filter 204, and are converged by the lens onto the image sensor 208. The image sensor 208 may collect or capture the light rays reflected or scattered by the surface to be detected to form an image of the surface to be detected.

At block 408, the image sensor 208 may transmit data of the image of the surface to be detected to one or more of relevant components or devices for processing.

In implementations, after obtaining data of the image of the surface to be detected, the image sensor 208 may transmit the data of the image of the surface to be detected the one or more processors 210. Additionally, or alternatively, the image sensor 208 may transmit the data of the image to the memory 212 for storage. Additionally, or alternatively, the image sensor 208 may transmit the data of the image to a device (such as the computing device 104) of a user (such as the user 108) via the network interface 216.

At block 410, the one or more processors 210 may process and analyze the data of the image.

In implementations, if the image sensor 208 transmits the data of the image of the surface to be detected to the one or more processors 210, the one or more processors 210 may process and analyze the data of the image. By way of example and not limitation, in an event that the surface to be detected is a skin surface such as a scalp surface, the one or more processors 210 may process and analyze the data of the image to identify hair and scalp conditions and textures of the skin surface, such as hair roots, skin secretions, troubles, hair dandruffs, etc.

At block 412, the memory 212 may store the data of the image of the surface to be detected into a designated storage space of the memory 212.

In implementations, if the image sensor 208 transmits the data of the image of the surface to be detected to the memory 212 for storage, the memory 212 may store the data of the image of the surface to be detected into a certain storage space of the memory 212, such as the database 220.

At block 414, the surface imaging system 102 may enable the device of the user or an application installed in the device of the user to display the image to the user.

In implementations, if the image sensor 208 transmits the data of the image of the surface to be detected to a device (e.g., the computing device 104) of a user, the surface imaging system 102 may enable the device of the user or an application installed in the device of the user to display the image to the user.

At block 416, the surface imaging system 102 may search for another image of the surface to be detected that has a desired degree of contrast.

In implementations, the surface imaging system 102 or the monitoring component 218 may receive an instruction from the user 108 via the computing device 104 to search for another image of the surface to be detected that has a desired degree of contrast. Additionally or alternatively, the one or more processors 210 of the surface imaging system 102 may be programmed to search for another image of the surface to be detected that has a desired degree of contrast.

In implementations, the surface imaging system 102 may search for another image of the surface to be detected that has a desired degree of contrast. By way of example and not limitation, the surface imaging system 102 may allow or cause the plurality of light sources 202 to change light frequencies of the light rays to be incident onto the surface to be detected. Additionally or alternatively, the surface imaging system 102 may allow or cause the plurality of light sources 202 to change intensities of the light rays to be incident onto the surface to be detected to increase a degree of contrast of an image of the surface to be detected.

Additionally or alternatively, the surface imaging system 102 may allow or cause the plurality of polarized filters 204 that are placed in front of the plurality of light sources 202 to change an orientation of polarization that the light rays to be incident onto the surface to be detected are allowed to pass through.

Additionally or alternatively, the surface imaging system 102 may allow or cause the plurality of light sources 202 to alter the angles of the light rays to be incident onto the surface to be detected to enable the image sensor 208 to obtain another image of the surface to be detected that has a higher or desired degree of contrast.

In implementations, each light source of the plurality of light sources 202 may include a plurality of light emitting diodes of different frequencies. Changing the light frequencies of the light rays to be incident onto the surface to be detected may include using a different light emitting diode of the plurality of light emitting diodes of different frequencies to generate light rays to be incident onto the surface to be detected.

In implementations, the surface imaging system 102 or the monitoring component 218 may enable a user (e.g., the user 108) to review the images of the surface to be detected, and receive instructions from the user 108 to cause the plurality of light sources 202 to change light frequencies and/or intensities of the light rays to be incident onto the surface to be detected, and/or cause the plurality of polarized filters 204 that are placed in front of the plurality of light sources 202 to change an orientation of polarization that the light rays to be incident onto the surface to be detected are allowed to pass through. In implementations, the surface imaging system 102 or the monitoring component 218 may transmit images of the surface to be detected to the device of the user to allow the user to examine the images of the surface to be detected, and to determine which image is desirable, i.e., which setting(s) (such as light frequencies and/or intensities of light rays generated by the plurality of light sources 202, an orientation of polarization allowed by the plurality of polarized filters 204, etc.) may produce desired image information of the surface to be detected.

Although the above method blocks are described to be executed in a particular order, in some implementations, some or all of the method blocks can be executed in other orders, or in parallel.

CONCLUSION

Although implementations have been described in language specific to structural features and/or methodological acts, it is to be understood that the claims are not necessarily limited to the specific features or acts described. Rather, the specific features and acts are disclosed as exemplary forms of implementing the claimed subject matter. Additionally or alternatively, some or all of the operations may be implemented by one or more ASICS, FPGAs, or other hardware.

The present disclosure can be further understood using the following clauses.

Clause 1: A system comprising: a plurality of light sources placed at one end of the system and configured to generate and direct light rays to be incident onto a surface to be detected at angles that are greater than or equal to a predetermined angle threshold, the predetermined angle threshold being set to ensure that images of the surface to be detected that have at least a predetermined degree of contrast are to be obtained; and an image sensor placed at another end of the system and configured to collect light rays reflected from the surface to be detected to form a first image of the surface to be detected.

Clause 2: The system of Clause 1, further comprising a processor configured to analyze the images of the surface to be detected that are transmitted from the image sensor.

Clause 3: The system of Clause 2, wherein the processor is further configured to calculate a degree of contrast of the first image of the surface to be detected.

Clause 4: The system of Clause 2, wherein the processor is further configured to instruct the plurality of light sources to alter the angles of the light rays to be incident onto the surface to be detected to enable the image sensor to obtain a second image of the surface to be detected, a degree of contrast of the second image being higher than a degree of contrast of the first image.

Clause 5. The system of Clause 2, wherein the processor is further configured to instruct the plurality of light sources to change intensities of the light rays to be incident onto the surface to be detected to increase a degree of contrast in the first image of the surface to be detected.

Clause 6: The system of Clause 2, wherein the processor is further configured to instruct the plurality of light sources to change light frequencies of the light rays to be incident onto the surface to be detected to capture a texture of the surface to be detected.

Clause 7: The system of Clause 6, wherein a light source of the plurality of light sources comprises a plurality of light emitting diodes of different frequencies, and wherein changing the light frequencies of the light rays to be incident onto the surface to be detected comprises using a different light emitting diode of the plurality of light emitting diodes of different frequencies to generate light rays to be incident onto the surface to be detected.

Clause 8: The system of Clause 2, further comprising a plurality of polarized filters separately placed in front of the plurality of light sources to allow a particular polarization of the light rays to be incident on the surface to be detected.

Clause 9: The system of Clause 8, wherein the processor is further configured to instruct the plurality of polarized filters to change an orientation of polarization to enable a different polarization of the light rays to be incident on the surface to be detected to obtain a second image of the surface to be detected, the second image having a different amount of geometric shadows than the first image.

Clause 10: The system of Clause 2, wherein the processor is further configured to search for an image of the surface to be detected that has a desired degree of contrast by instructing the plurality of light sources to change light frequencies and intensities of the light rays to be incident onto the surface to be detected, and instructing a plurality of polarized filters that are placed in front of the plurality of light sources to change an orientation of polarization that the light rays to be incident onto the surface to be detected are allowed to pass through.

Clause 11: The system of Clause 1, wherein the surface to be detected comprises a surface that is partially transparent to a certain range of light frequencies, different light frequencies of the certain range of light frequencies leading to different degrees of transparency of the surface to be detected.

Clause 12: The system of Clause 1, wherein the surface to be detected comprises a skin surface of a human.

Clause 13: The system of Clause 1, further comprising an optical lens configured to focus the light rays reflected from the surface to be detected onto the image sensor.

Clause 14: The system of Clause 1, further comprising a monitoring component configured to enable a user to review the images of the surface to be detected, and receive instructions from the user to cause the plurality of light sources to change light frequencies and/or intensities of the light rays to be incident onto the surface to be detected, and/or cause a plurality of polarized filters that are placed in front of the plurality of light sources to change an orientation of polarization that the light rays to be incident onto the surface to be detected are allowed to pass through.

Clause 15: A method implemented by a surface imaging system, the method comprising: generating and directing, by a plurality of light sources placed at one end of the surface imaging system, light rays to be incident onto a surface to be detected at angles that are greater than or equal to a predetermined angle threshold, the predetermined angle threshold being set to ensure that images of the surface to be detected that have at least a predetermined degree of contrast are to be obtained; and collecting, by an image sensor placed at another end of the surface imaging system, light rays reflected from the surface to be detected to form a first image of the surface to be detected.

Clause 16: The method of Clause 15, further comprising: altering, by the plurality of light sources, the angles of the light rays to be incident onto the surface to be detected to enable the image sensor to obtain a second image of the surface to be detected, a degree of contrast of the second image being higher than a degree of contrast of the first image.

Clause 17: The method of Clause 15, further comprising: changing, by the plurality of light sources, intensities of the light rays to be incident onto the surface to be detected to increase a degree of contrast in the first image of the surface to be detected; and/or changing, by the plurality of light sources, light frequencies of the light rays to be incident onto the surface to be detected to capture a texture of the surface to be detected.

Clause 18: The method of Clause 15, further comprising: searching for an image of the surface to be detected that has a desired degree of contrast by allowing the plurality of light sources to change light frequencies and intensities of the light rays to be incident onto the surface to be detected, and allowing a plurality of polarized filters that are placed in front of the plurality of light sources to change an orientation of polarization that the light rays to be incident onto the surface to be detected are allowed to pass through.

Clause 19: The method of Clause 15, further comprising: enabling a user to review the images of the surface to be detected, and receive instructions from the user to cause the plurality of light sources to change light frequencies and/or intensities of the light rays to be incident onto the surface to be detected, and/or cause a plurality of polarized filters that are placed in front of the plurality of light sources to change an orientation of polarization that the light rays to be incident onto the surface to be detected are allowed to pass through.

Clause 20: One or more computer readable media storing executable instructions that, when executed by one or more processors of a surface imaging system, cause the one or more processors to perform acts comprising: causing a plurality of light sources placed at one end of the surface imaging system to generate and direct light rays to be incident onto a surface to be detected at angles that are greater than or equal to a predetermined angle threshold, the predetermined angle threshold being set to ensure that images of the surface to be detected that have at least a predetermined degree of contrast are to be obtained; and causing an image sensor placed at another end of the surface imaging system to collect light rays reflected from the surface to be detected to form a first image of the surface to be detected.

What is claimed is:

1. A surface imaging system comprising:
   a plurality of light sources individually placed in different positions at an end of the surface imaging system and configured to generate and direct light rays to be incident onto a surface to be detected at angles that are greater than or equal to a predetermined angle threshold, the predetermined angle threshold being set to ensure that images of the surface to be detected that have at least a predetermined degree of contrast are to be obtained;
   a plurality of polarized filters separately placed in front of the plurality of light sources to allow a particular polarization of the light rays to be incident on the surface to be detected;
   an image sensor placed at another end of the surface imaging system and configured to collect light rays reflected from the surface to be detected to form images of the surface to be detected; and
   a processor configured to search for a first image of the surface to be detected that has a desired degree of contrast by instructing the plurality of light sources to change light frequencies and intensities of the light rays to be incident onto the surface to be detected, and instructing the plurality of polarized filters to change an orientation of polarization that the light rays to be incident onto the surface to be detected are allowed to pass through, wherein changing the light frequencies of the light rays to be incident onto the surface to be detected comprises using different light emitting diodes of different frequencies to generate the light rays to be incident onto the surface to be detected.

2. The surface imaging system of claim 1, wherein the processor is further configured to analyze the images of the surface to be detected that are transmitted from the image sensor.

3. The surface imaging system of claim 2, wherein the processor is further configured to calculate a degree of contrast of the first image of the surface to be detected.

4. The surface imaging system of claim 2, wherein the processor is further configured to instruct the plurality of light sources to alter the angles of the light rays to be incident onto the surface to be detected to enable the image sensor to obtain a second image of the surface to be detected, a degree of contrast of the second image being higher than a degree of contrast of the first image.

5. The surface imaging system of claim 2, wherein the processor is further configured to instruct the plurality of light sources to change the intensities of the light rays to be incident onto the surface to be detected to increase a degree of contrast in the first image of the surface to be detected.

6. The surface imaging system of claim 2, wherein the processor is further configured to instruct the plurality of light sources to change the light frequencies of the light rays to be incident onto the surface to be detected to capture a texture of the surface to be detected.

7. The surface imaging system of claim 1, wherein the processor is further configured to instruct the plurality of polarized filters to change the orientation of polarization to enable a different polarization of the light rays to be incident on the surface to be detected to obtain a second image of the surface to be detected, the second image having a different amount of geometric shadows than the first image.

8. The surface imaging system of claim 1, wherein the surface to be detected comprises a surface that is partially transparent to a certain range of light frequencies, different light frequencies of the certain range of light frequencies leading to different degrees of transparency of the surface to be detected.

9. The surface imaging system of claim 1, wherein the surface to be detected comprises a skin surface of a human.

10. The surface imaging system of claim 1, further comprising an optical lens configured to focus the light rays reflected from the surface to be detected onto the image sensor.

11. The surface imaging system of claim 1, further comprising a monitoring component configured to enable a user to review the images of the surface to be detected, and receive instructions from the user to cause the plurality of light sources to change the light frequencies and/or intensities of the light rays to be incident onto the surface to be detected, and/or cause the plurality of polarized filters to change the orientation of polarization that the light rays to be incident onto the surface to be detected are allowed to pass through.

12. The surface imaging system of claim 1, further comprising:
   a body portion; and
   a tip portion attached to the body portion, wherein:
      the plurality of light sources and the plurality of polarized filters are deployed at a first end of the tip portion, and
      the image sensor is deployed in the body portion.

13. A method implemented by a surface imaging system, the method comprising:
   generating and directing, by a plurality of light sources individually placed in different positions at an end of the surface imaging system, light rays to be incident onto a surface to be detected at angles that are greater than or equal to a predetermined angle threshold, the predetermined angle threshold being set to ensure that images of the surface to be detected that have at least a predetermined degree of contrast are to be obtained;
   collecting, by an image sensor placed at another end of the surface imaging system, light rays reflected from the surface to be detected to form images of the surface to be detected; and
   searching for a first image of the surface to be detected that has a desired degree of contrast by instructing the plurality of light sources to change light frequencies and intensities of the light rays to be incident onto the surface to be detected, and instructing a plurality of polarized filters that are separately placed in front of the plurality of light sources to change an orientation of polarization that the light rays to be incident onto the surface to be detected are allowed to pass through, wherein changing the light frequencies of the light rays to be incident onto the surface to be detected comprises using different light emitting diodes of different frequencies to generate the light rays to be incident onto the surface to be detected.

14. The method of claim 13, further comprising: altering, by the plurality of light sources, the angles of the light rays to be incident onto the surface to be detected to enable the image sensor to obtain a second image of the surface to be detected, a degree of contrast of the second image being higher than a degree of contrast of the first image.

15. The method of claim 13, further comprising:
changing, by the plurality of light sources, the intensities of the light rays to be incident onto the surface to be detected to increase a degree of contrast in the first image of the surface to be detected; and/or
changing, by the plurality of light sources, the light frequencies of the light rays to be incident onto the surface to be detected to capture a texture of the surface to be detected.

16. The method of claim 13, further comprising:
enabling a user to review the images of the surface to be detected, and receive instructions from the user to cause the plurality of light sources to change the light frequencies and/or the intensities of the light rays to be incident onto the surface to be detected, and/or cause the plurality of polarized filters to change the orientation of polarization that the light rays to be incident onto the surface to be detected are allowed to pass through.

17. One or more computer readable media storing executable instructions that, when executed by one or more processors of a surface imaging system, cause the one or more processors to perform acts comprising:
causing a plurality of light sources individually placed in different positions at an end of the surface imaging system to generate and direct light rays to be incident onto a surface to be detected at angles that are greater than or equal to a predetermined angle threshold, the predetermined angle threshold being set to ensure that images of the surface to be detected that have at least a predetermined degree of contrast are to be obtained; and
causing an image sensor placed at another end of the surface imaging system to collect light rays reflected from the surface to be detected to form images of the surface to be detected; and
searching for a first image of the surface to be detected that has a desired degree of contrast by instructing the plurality of light sources to change light frequencies and intensities of the light rays to be incident onto the surface to be detected, and instructing a plurality of polarized filters that are separately placed in front of the plurality of light sources to change an orientation of polarization that the light rays to be incident onto the surface to be detected are allowed to pass through, wherein changing the light frequencies of the light rays to be incident onto the surface to be detected comprises using different light emitting diodes of different frequencies to generate the light rays to be incident onto the surface to be detected.

* * * * *